United States Patent [19]

Martin Ramon et al.

[11] Patent Number: 5,179,228
[45] Date of Patent: Jan. 12, 1993

[54] PREPARATION OF N-PHOSPHONOMETHYLGLYCINE BY OXIDATION OF N-PHOSPHONOMETHYLIMINODIACETIC ACID

[75] Inventors: Juan L. Martin Ramon, Madrid; Julio Muñoz Madroñero, Cerceda, both of Spain

[73] Assignee: Ercros S.A., Barcelona, Spain

[21] Appl. No.: 778,842

[22] PCT Filed: Mar. 12, 1991

[86] PCT No.: PCT/ES91/00013
§ 371 Date: Dec. 18, 1991
§ 102(e) Date: Dec. 18, 1991

[87] PCT Pub. No.: WO91/13893
PCT Pub. Date: Sep. 19, 1991

[51] Int. Cl.$^5$ ............................................. C07F 9/38
[52] U.S. Cl. ............................................. 562/17
[58] Field of Search ................................. 562/17

[56] References Cited

U.S. PATENT DOCUMENTS

| 4,147,719 | 4/1979 | Franz | 260/501.12 |
| 4,579,689 | 4/1986 | Hershman et al. | 260/502.5 F |
| 4,582,650 | 4/1986 | Felthouse | 260/502.5 F |
| 4,952,723 | 8/1990 | Fields, Jr. et al. | 562/17 |
| 4,965,402 | 10/1990 | Riley et al. | 562/17 |

Primary Examiner—Jose G. Dees
Assistant Examiner—Porfirlo Nazario
Attorney, Agent, or Firm—Henry M. Bissell

[57] ABSTRACT

Improvements to a method for preparing N-phosphonomethylglycyne by oxidation of N-phosphonomethyliminodiacetic acid. N-phosphonomethylglycine may be obtained by oxidation of N-phosphonomethyliminodiacetic acid with $O_2$ or with an oxygen-containing gas, in the presence of a noble metal catalyst on activated carbon. To avoid the catalyst losses, the improvements of the invention consist in a pressure scavaging with $N_2$, after completion of the oxidation reaction. Owing to such treatment, the catalyst losses are reduced from 30% to 1%, making the processing economically viable on a large industrial scale. The recovered catalyst holds its catalytic activity and may be reused at least 20 consecutive times. N-phosphonomethylglycine is a herbicide of extended application.

4 Claims, No Drawings

5,179,228

PREPARATION OF N-PHOSPHONOMETHYLGLYCINE BY OXIDATION OF N-PHOSPHONOMETHYLIMINODIACETIC ACID

FIELD OF THE INVENTION

The invention relates to improvements introduced into a method of obtaining N-phosphonomethylglycine by oxidation of N-phosphonomethyliminodiacetic acid with oxygen or a gas containing oxygen, utilising as catalyst a noble metal supported on activated carbon. Specifically, the improvements of the invention relate to a treatment directed towards minimising the loss of the noble metal catalyst which occurs in this type of reaction.

ANTECEDENTS OF THE INVENTION

N-phosphonomethylglycine, described in the U.S. Pat. No. 3,799,758, is a known herbicide and its use is very widespread. Since its appearance on the market, various methods for obtaining it have been described and patented. One of these methods, specifically, the one claimed in the Spanish Patent No. 415.335 in the name of the Monsanto Company (equivalent to the U.S. Pat. No. 258,281, on May 5, 1972) provides a method of obtaining N-phosphonomethylglycine by oxidation of N-phosphonomethyliminodiacetic acid with oxygen or a gas containing oxygen, utilising a noble metal (Pd, Pt, Rh) supported on activated carbon as catalyst for the reaction. Although this method allows for obtaining N-phosphonomethylglycine in acceptable yield and state of purity, it has the disadvantage that the losses of the noble metal used as catalyst are so great (may be as much as 30%) that said method is not economically profitable and that the losses of the noble metal increase the price of the finished product to such an extent that the method is not viable on an industrial scale.

On the other hand, it is a fact known by the technical experts in catalysis that the losses of the noble metal which occur in the both acidic and basic catalytic methods, is by dissolution of said metal in the reaction water, thus requiring a complex and costly treatment to recover said metal. Consequently, this type of method is not viable in practice for obtaining finished products with slightly increased value.

Therefore it would be advantageous to have available a method which allows for obtaining N-phosphonomethylglycine of sufficient purity in good yield by oxidation of N-phosphonomethyliminodiacetic in the presence of a noble metal catalyst which overcomes the disadvantages referred to previously. In particular, it would be advantageous for this method to minimise the losses of noble metal used as catalyst in such a way that they do not substantially increase the cost of the finished product, with the object of rendering this method industrially viable.

Consequently, an object of the invention is the introduction of improvements over the known methods of obtaining N-phosphonomethylglycine by oxidation of N-phosphonomethyliminodiacetic acid with oxygen, in the presence of a noble metal supported on activated carbon as catalyst, providing that said improvements minimise the losses of noble metal, by means of implementation of a treatment intended to recover practically the total amount of the catalyst utilised, without loss of its catalytic activity.

BRIEF DESCRIPTION OF THE INVENTION

The improvements of the invention may be stated as specifically to minimise the losses of the noble metal catalyst used for obtaining N-phosphonomethylglycine by oxidation of N-phosphonomethyliminodiacetic acid. For minimising these losses, the invention proposes effecting a flushing-out with nitrogen once the oxidation reaction is completed.

Due to this, it follows that the content of noble metal in the reaction solution is less than 1 ppm, compared with a content of said metal greater than 70 ppm which is present in said solution if the flushing-out with nitrogen is not effected. Therefore, this flushing-out with nitrogen minimises the losses, lowering the percentage loss from 30% to less than 1%, in this way making this type of method economically viable. The obtaining of these improvements will be referred to in detail in the following description.

DETAILED DESCRIPTION OF THE INVENTION

The invention provides a series of betterments or improvements directed towards minimising the losses of noble metal used as catalyst in the known method for obtaining N-phosphonomethylglycine by oxidation of N-phosphonomethyliminodiacetic acid. In the prior Patent cited in the antecedents for the invention, a method for obtaining N-phosphonomethylglycine is described which may be characterised in accordance with the following equation in which, for the sake of simplicity, palladium on carbon Pd/C is used as the catalyst:

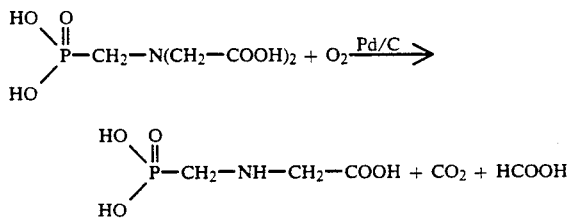

The reaction is carried out in the temperature range between 25° C. and 125° C., preferable between 90° C. and 105° C., at a pressure in the range between 1 and 5 kg/cm$^2$. However, for the reasons indicated previously, the method disclosed in said Patent is not viable on the industrial scale. In order for said method to become industrially viable, the losses of catalyst would need to be minimised.

Therefore an economical and simple form of said method has been sought to render it industrially viable. This has resulted from making use of the improvements provided by the present invention. These improvements consist of effecting a treatment of the reaction solution once the reaction has been completed to recover practically the total amount of the catalyst utilised, without alteration of its catalytic activity and capability of being re-utilised to catalyse this type of reaction without varying the yields. Consequently, in a first phase, the oxidation of N-phosphonomethyliminodiacetic acid with oxygen or a gas containing oxygen is carried out in the presence of a noble metal catalyst supported on activated carbon and, once this reaction is completed, the reaction solution obtained is flushed-out with nitrogen under pressure for the purpose of recovering the noble metal in accordance with the method of operation to be described later.

For carrying on the oxidation reaction to completion, it has been found that it is advantageous to carry on said reaction at a temperature in the range between 100° C. and 105° C., at a pressure in the range between 3 and 4 kg/cm$^2$, using water as the solvent at a pH value in the range between 4 and 8, with the best results being obtained at a pH value close to 7.

The initial concentration of N-phosphonomethyliminodiacetic acid should be in the range between 4% and 15% by weight, preferably between 4% and 6% by weight, because higher concentrations diminish the yield from the reaction and lower concentrations diminish the productivity. The percentage of catalyst calculated with respect to the N-phosphonomethyliminodiacetic acid may be varied between 4% and 10% by weight, although with a mean percentage of 6% it is possible to obtain very good results. For implementation of this invention, palladium on carbon (Pd/C) has been used as the catalyst.

Once the oxidation reaction has been completed, with the object of minimising the loss of the noble metal, the treatment which follows, and which constitutes the improvement provided by the present invention, is carried out. Said treatment may be summed up as being that, in a single phase after completion of the reaction in an atmosphere of oxygen, or of a gas containing oxygen, the reaction solution obtained is de-pressurised and is flushed-out twice with nitrogen, with the object of removing as much oxygen as possible from the reaction solution. Following this, the reaction vessel is re-pressurised with nitrogen, at a pressure in the range between 0.5 kg/cm$^2$ and 5 kg/cm$^2$, preferably between 1 and 2 kg/cm$^2$ and, maintaining this pressure, the passage of nitrogen is continued at a flow rate from 10 to 30 liters/minute, during a period of time lasting from 15 minutes up to 1 hour. Obviously, the flow rate (liters/minute) of nitrogen depends upon the scale of the process. The period of time of passing-in the nitrogen is a function of the temperature of the reaction solution, which may be between 20° C. and 120° C., since the reaction mixture, when pressurised with nitrogen could heat up or, alternatively this treatment could be carried out at the temperature of the oxidation reaction without the necessity of heating the reaction solution. It has been found that, with a temperature of the reaction solution of 115° C., the period of time for the passage of nitrogen is 30 minutes in order to obtain a content of 0.9 ppm of palladium in said solution and that, at a temperature of 100° C., the period of time for the passage of nitrogen is 45 minutes in order to obtain a content of 0.6 ppm of palladium in said solution. When the content of palladium in the reaction solution is less than 1 ppm, determined by atomic absorption, the reaction vessel is de-pressurised, the catalyst is filtered off for later use and the filtrate obtained in concentrated in vacuo. The N-phosphonomethylglycine is obtained by recrystallisation.

If this treatment is not carried out, then the content of palladium in the reaction solution is greater than 70 ppm, as is evident in the examples which accompany this description. These losses of noble metal greater than 70 ppm lead to an increase in cost of the finished product beyond the limits of economic viability.

However, by means of the treatment, proposed by this invention of the reaction solution once the reaction is completed, the losses of noble metal in the solution are minimised, and make viable, in a simple manner, a method which was not carried out in the procedures referred to earlier. Furthermore, the recovered catalyst maintains it catalytic activity and may be re-utilised at least for 20 consecutive times without loss of its activity and without altering the yields.

Consequently, by means of the improvements due to this invention, it is possible to obtain N-phosphonomethylglycine by oxidation of N-phosphonomethyliminodiacetic acid, at the industrial level with an adequate purity and yield and, furthermore, it is possible to recover the noble metal catalyst used, without loss of its catalytic activity by means of a simple treatment which does not require the installation of complex equipment.

The present invention will be clearly illustrated with the following examples which are not to be considered as limitative in any way.

EXAMPLE 1

In a stainless-steel (AISI 316) autoclave reactor of 40 liters capacity, there are introduced in the following order: 2.045 Kg of N-phosphonomethyliminodiacetic acid of 97% purity, 33.974 Kg of water at a pH value of ca. 7, and 121.5 grams of dry catalyst (commercial) of 5% palladium on carbon, which represents 6.075 grams of pure palladium by assay.

Following this, the passing in of oxygen is continued until an internal pressure of 3.6-3.8 kg/cm$^2$ is reached and the mixture heats up, maintaining the given pressure until a temperature of 100° C. is reached, having oxygen passed through the mixture at a flow rate of 2.5 liters/minute. The suspension is stirred continuously under these conditions for a period of 2 hours. When the stated period of time has elapsed, a sample is taken and, after the catalyst has been removed by filtration, is analysed for the content of N-phosphonomethyliminodiacetic and the ppm of palladium present, finding 110 ppm. When it is confirmed that at least 95 of the starting material has been converted, the supply of oxygen is cut off and the reactor is de-pressurised, changing over to pressurisation this time with nitrogen up to a pressure of 2 Kg/cm$^2$ and the reaction solution is heated to 115° C., maintaining this condition with bubbles of nitrogen through the reaction mixture at a flow rate of 24 liters/minute during a period of time of at least 30 minutes. When the treatment is completed and it has been shown that the reaction solution at this moment has a palladium content of less than 1 ppm (0.9 ppm), the preceding treatment is terminated and the reactor is de-pressurised, the catalyst is filtered off and the filtrate obtained is later concentrated in vacuo and the N-phosphonomethylglycine is obtained by re-crystallisation. The yield of N-phosphonomethylglycine having a degree of purity greater than 97% was 1.449 kg. (yield 96.4%).

EXAMPLE 2

This experiment was carried out to determine the influence of temperature on the process of recovery of the palladium dissolved in the reaction solution. The experiment was carried out with the same method utilised for the reaction in Example 1. With regard to the treatment after the reaction for recovery of the palladium, this was carried out at a temperature equal to that of the reaction (100° C.) and the time employed so that the dissolved palladium was less than 1 ppm (0.6 ppm) in the reaction water was 45 minutes.

The yield of N-phosphonomethylglycine having a degree of purity greater than 97% was 1.440 Kg (yield 95.6%).

Having described the object of the present invention, it is declared that what constitutes the essential nature of the same is that which is stated in the following Claims.

We claim:

1. Improvements introduced into a method of obtaining N-phosphonomethylglycine by oxidation of N-phosphonomethyliminodiacetic acid with oxygen or a gas containing oxygen, in the presence of a catalyst of noble metal supported on activated carbon, said improvements being characterised in that, once the reaction has been completed and before proceeding with its cooling, a flushing-out with nitrogen under slight pressure is carried out, at a temperature equal to, or greater than that of the reaction, for a definite period of time, which determines the reduction of the losses of noble metal in the solution.

2. The improvements according to claim 1, characterised in that the passing-in of nitrogen is effected at a temperature in the range between 20° C. and 120° C.

3. The improvements according to claim 1, characterised in that the passing-in of nitrogen is carried on for a period of time lasting from 15 minutes up to 1 hour.

4. The improvements according to claim 1, characterised in that the pressure of the reaction solution during the passing-in of nitrogen is in the range between 0.5 kg/cm$^2$ and 5 kg/cm$^2$.

* * * * *